United States Patent [19]
Silvestrini et al.

[11] Patent Number: 5,645,582
[45] Date of Patent: *Jul. 8, 1997

[54] OVERLAPPING RING DEVICE FOR CORNEAL CURVATURE ADJUSTMENT

[75] Inventors: Thomas Silvestrini, Alamo; Mark Mathis, Fremont, both of Calif.

[73] Assignee: KeraVision, Inc., Fremont, Calif.

[*] Notice: The term of this patent shall not extend beyond the expiration date of Pat. No. 5,323,788.

[21] Appl. No.: 392,911

[22] PCT Filed: Sep. 16, 1993

[86] PCT No.: PCT/US93/08770

§ 371 Date: Feb. 28, 1995

§ 102(e) Date: Feb. 28, 1995

[87] PCT Pub. No.: WO94/06381

PCT Pub. Date: Mar. 31, 1994

[51] Int. Cl.$^6$ ............................................. A61F 2/14
[52] U.S. Cl. ............................................. 623/5; 606/166
[58] Field of Search ........................... 623/4, 5; 606/107, 606/166, 167

[56] References Cited

U.S. PATENT DOCUMENTS

| | | | |
|---|---|---|---|
| 4,452,235 | 6/1984 | Reynolds | 606/107 X |
| 4,655,774 | 4/1987 | Choyce | 623/5 |
| 4,671,276 | 6/1987 | Reynolds | 606/166 |
| 4,688,570 | 8/1987 | Kramer et al. | |
| 4,782,820 | 11/1988 | Woods | |
| 4,815,463 | 3/1989 | Hanna | |
| 4,941,093 | 7/1990 | Marshall et al. | |
| 4,961,744 | 10/1990 | Kilmer et al. | 606/166 |
| 4,976,719 | 12/1990 | Siepser | |
| 5,066,301 | 11/1991 | Wiley | |
| 5,090,955 | 2/1992 | Simon | 606/166 X |
| 5,098,443 | 3/1992 | Parel et al. | 623/4 |
| 5,300,118 | 4/1994 | Silvestrini et al. | 623/5 |
| 5,323,788 | 6/1994 | Silvestrini et al. | 623/5 X |
| 5,372,580 | 12/1994 | Simon et al. | 606/107 X |

OTHER PUBLICATIONS

English translation of Brazilian Patent Application No. BR 8705060 (Mar. 21, 1989).

Hartmann Chr., et al., "Intrastromale Implantation Eines Justierbaren Kunstsoffringes Zur Hornhautrefraktionsänderung", *Kongreβ der Deutschen Gesellschaft für Intraokularlinsen Implantation*, delivered by H. Freyler et al., Springer–Verlag, Wien, pp. 465–475. The corresponding English language translation of the article was authored by Hartmann, Chr., et al., entitled Intrastromal implantation of an adjustable plastic ring to alter the corneal refraction *Congress for German Society for Intraocular Lens Implantation*, delivered by H. Freyler et al., (7 pages total).

Simón, G., et al., "Long term in vivo topographic studies of gel injection adjustable keratoplasty (GIAK)" *Abstracts: The Association for Research in Vision and Ophthalmology*, Annual Meeting Abstract Issue, Sarasota, Florida, USA, May 2–May 7, 1993, p. 1248, (abstract 2679–52).

Simón, G., et al., "Refractive remodeling of the cornea by intrastromal rings" *Abstracts: Eighth International Congress of Eye Research*, Proceedings of the International Society for Eye Research, San Francisco, California, USA, Sep. 4–8, 1988, vol. V, (abstract No. 47).

(List continued on next page.)

*Primary Examiner*—Mary Beth Jones
*Attorney, Agent, or Firm*—Morrison & Foerster LLP

[57] ABSTRACT

The intrastromal corneal ring (ICR) (47) of the invention has a flexible, preferably circular body sized and configured such that it can be inserted into a human eye and comprised of a material which is compatible with human ocular tissue. The end portions (48 and 49) of the circular body overlap each other and are formed in several different configurations or embodiments. The end portions (48 and 49) are preferably configured such that when allowed to come together they inter-mesh and provide a ring with a smooth and continuous outer profile.

10 Claims, 8 Drawing Sheets

OTHER PUBLICATIONS

Simón, G., et al., "Refractive remodeling of the cornea by intrastromal rings" *The Association for Research in Vision and Ophthalmology*, Annual Spring Meeting, Sarasota, Florida, USA, Apr. 30–May 5, 1989, p. 187, (abstract 43).

Blavatskaia, D.E.D., "The use of intralamellar homoplasty in order to reduce refraction of the eye" *Überstzt. Aus. Ofalmol. Zh.* (1966) 7:530–537 which was apparently translated to *Arch. Soc. Ophthmol. Optom.* (1988) 6:31–325. A complete English translation was previously enclosed.

OVERLAPPING RING DEVICE FOR CORNEAL CURVATURE ADJUSTMENT

FIELD OF THE INVENTION

This invention is in the general field of medical technology and relates specifically to an intrastromal corneal ring having overlapping or connected ends for varying corneal curvature to correct vision.

BACKGROUND OF THE INVENTION

Anomalies in the shape of the eye and specifically the shape as defined in part by the corneal can cause visual disorders. Hyperopia occurs when the eyeball is too short. In such a case, parallel rays from greater than 20 feet focus behind the retina. Myopia, on the other hand occurs when the eyeball is too long. The focus of parallel rays in this case is in front of the retina. Astigmatism is a condition in which the parallel rays of light do not come to a single point, but rather have a variable focus due to the fact that the cornea is aspherical and refracts light in a different meridian at different distances. Some degree of astigmatism is normal, but where it is too high, it must be corrected in order to provide acceptable vision.

Conditions such as hyperopia, myopia and astigmatism are usually corrected by glasses or contact lenses. Surgical methods for the correction of such disorders have been cited in the literature and include radial keratotomy (see e.g. U.S. Pat. Nos. 4,815,463 and 4,688,570) and laser corneal ablation (see e.g. U.S. Pat. No. 4,941,093). Further, the general method of implanting rings in the corneal stroma to change the curvature of the cornea is known. Previous work involving the implantation of polymethylmethacrylate (PMMA) rings, allograft corneal tissue and hydrogels is well documented. One of the ring devices involves a ring design that allows a split ring to be inserted into a channel. The channel is formed by dissecting the stromal layer of the cornea using a minimally invasive incision. Thereafter, the implant is inserted into the channel and the channel is sutured shut.

U.S. Pat. No. 4,452,235, which is herein incorporated by reference in its entirety, describes a method and apparatus for corneal curvature adjustment. The method involves inserting one end of a split end adjusting ring into the cornea of the eye and moving the ring in a circular path until its ends meet. The ends are thereafter adjusted relative to each other so that the ends can be connected. When the correct size ring is inserted the eye will have been caused to assume the correct curvature.

Other devices for adjusting the corneal curvature have been disclosed such as the device shown within U.S. Pat. No. 4,671,276 issued Jun. 9, 1987. In addition, devices for affecting other parts of the eye such as an iris retaining device are disclosed within U.S. Pat. No. 4,782,820 issued Nov. 8, 1988 and a variable focus lens which is disclosed within U.S. Pat. No. 5,066,301 issued Nov. 19, 1991. More recently a method of changing cornea curvature by injecting a gel into the cornea was disclosed in U.S. Pat. No. 5,090,955 issued Feb. 25, 1992.

The present invention describes split ring devices which have end structures and configurations which provide certain advantages and improvements as compared to earlier ring structures.

SUMMARY OF THE INVENTION

The present invention is an intrastromal corneal ring (ICR) comprised of an elongated, flexible, circular body member. The ICR is of a size and shape such that it can be inserted into a human eye and specifically into the outer periphery of the cornea of a human eye. The ICR is comprised of a material which is compatible with human ocular tissue and specifically compatible with corneal tissue. The end portions of the body member may be formed in several different configurations or embodiments. The end portions overlap each other and are preferably configured such that when they are forced toward each other horizontally and/or vertically they intermesh and provide a tight fit against each other. Further, the ends are preferably configured in such a manner that when allowed to come together the resulting ring provides a smooth and continuous outer profile.

A primary object of the invention is to provide an ICR with overlapping end portions.

An advantage of the invention is that a closed circuit ring is provided without the need to attach the ends with sutures, additional component fasteners or interconnecting means.

A feature of the invention is that when the ring is in place, it provides a continuous, smooth outer profile.

Another advantage of the ring is that it can be easily inserted into the corneal tissue of the eye and thereafter released in a manner whereby the ends of the ring will seal themselves together due to the torsional forces provided by the elongated body of the ring.

These and other objects, advantages and features of the present invention will become apparent to those persons skilled in the art upon reading the details of the structure and use as more fully set forth below, reference being made to the accompanying drawings forming a part hereof.

BRIEF DESCRIPTION OF THE DRAWINGS

FIG. 7 is a cross sectional view showing split overlapping ring ends while

FIG. 8 is a perspective view showing overlapping ring ends with the details being shown in FIG. 8A while FIGS. 8B, 8C and 8D are cross sectional subembodiments of the embodiment shown in FIG. 8 while

FIG. 12 shows notched interlocking embodiments in FIGS. 12A and 12B.

DETAILED DESCRIPTION OF THE INVENTION

Before the intrastromal corneal ring and its various configurations are described, it is to be understood that this invention is not limited to the particular embodiments, configurations and materials described as such may, of course, vary. It is also to be understood that the terminology used herein is for the purpose of describing particular embodiments only and is not intended to be limiting, since the scope of the present invention will be limited only by the appended claims.

The basic structure function and operation of the intrastromal corneal rings of the invention is shown and discussed in connection with FIGS. 1–6. FIGS. 7–13 show seven different embodiments of the invention which show seven basic configurations whereby the ring ends can be connected to each other without the use of additional components in a manner so as to provide a smooth and continuous interconnection between the ends so that the surface of the ring appears substantially smooth and continuous along its entire surface even at the interconnection of the ring ends. The different embodiments shown in FIGS. 7–13 can each include a number of different subembodiments by varying other parameters such as the cross sectional surface dimensions of the ring e.g. forming the ring from cross sections in the form of a circle, square, rectangle, triangle, oval, etc. Although a number of these configurations are shown others are possible and are contemplated by this invention. Further, other possible interconnections are contemplated by this invention with the proviso that preferred interconnections do not include an additional component for interconnecting the end portions of the ring and further provided that the interconnections provide for a substantially smooth and continuous interconnection of the ring ends.

Before discussing these specific embodiments of FIGS. 7–13 the general structure and method of use of intrastromal corneal rings will be described in connection with FIGS. 1–4 and thereafter generalized information relating to the rings of the present invention in connection with FIGS. 5 and 6.

Figure 1:
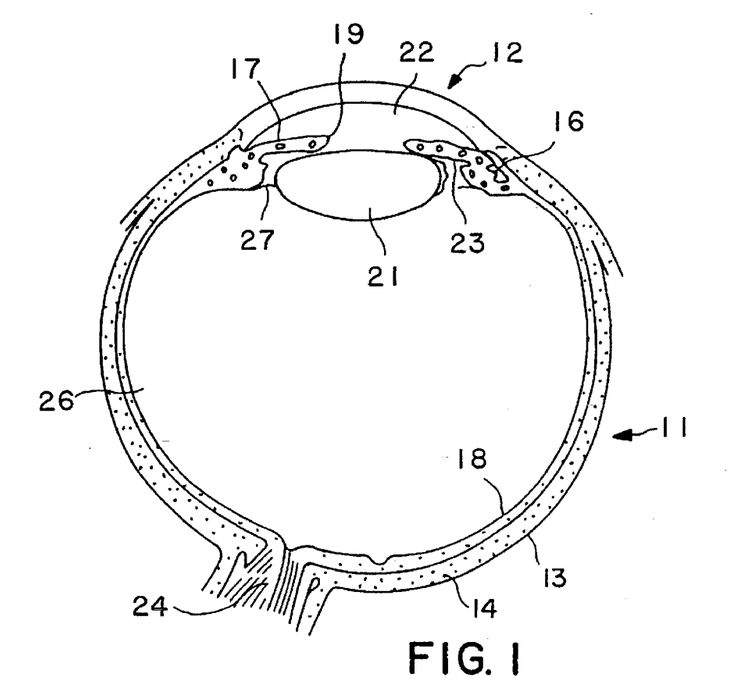
FIG. 1 is a schematic representation of a horizontal section of the eye.

FIG. 1 shows a horizontal section of the eye with the globe 11 of the eye resembling a sphere with an anterior bulged spherical portion representing the cornea 12. The globe 11 of the eye consists of three concentric coverings enclosing the various transparent media through which the light must pass before reaching the sensitive retina 18. The outermost covering is a fibrous protective portion the posterior five-sixths of which is white and opaque and called the sclera 13, and sometimes referred to as the white of the eye where visible to the front. The anterior one-sixth of this outer layer is the transparent cornea 12.

A middle covering is mainly vascular and nutritive in function and is comprised of the choroid 14, ciliary body 16 and iris 17. The choroid 14 generally functions to maintain the retina 18. The ciliary body 16 is involved in suspending the lens 21 and accommodation of the lens. The iris 17 is the most anterior portion of the middle covering of the eye and is arranged in a frontal plane. It is a thin circular disc corresponding to the diaphragm of a camera, and is perforated near its center by a circular aperture called the pupil 19. The size of the pupil varies to regulate the amount of light which reaches the retina 18. It contracts also to accommodation, which serves to sharpen the focus by diminishing spherical aberration. The iris 17 divides the space between the cornea 12 and the lens 21 into an anterior chamber 22 and posterior chamber 23. The innermost portion of covering is the retina 18, consisting of nerve elements which form the true receptive portion for visual impressions.

The retina 18 is a part of the brain arising as an outgrowth from the fore-brain, with the optic nerve 24 serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body 26 is a transparent gelatinous mass which fills the posterior four-fifths of the globe 11. At its sides it supports the ciliary body 16 and the retina 18. A frontal saucer-shaped depression houses the lens.

The lens 21 of the eye is a transparent biconvex body of crystalline appearance placed between the iris 17 and vitreous body 26. Its axial diameter varies markedly with accommodation. A ciliary zonule 27, consisting of transparent fibers passing between the ciliary body 16 and lens 21 serves to hold the lens 21 in position and enables the ciliary muscle to act on it.

Referring again to the cornea 12, this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place through the cornea.

Figure 2:
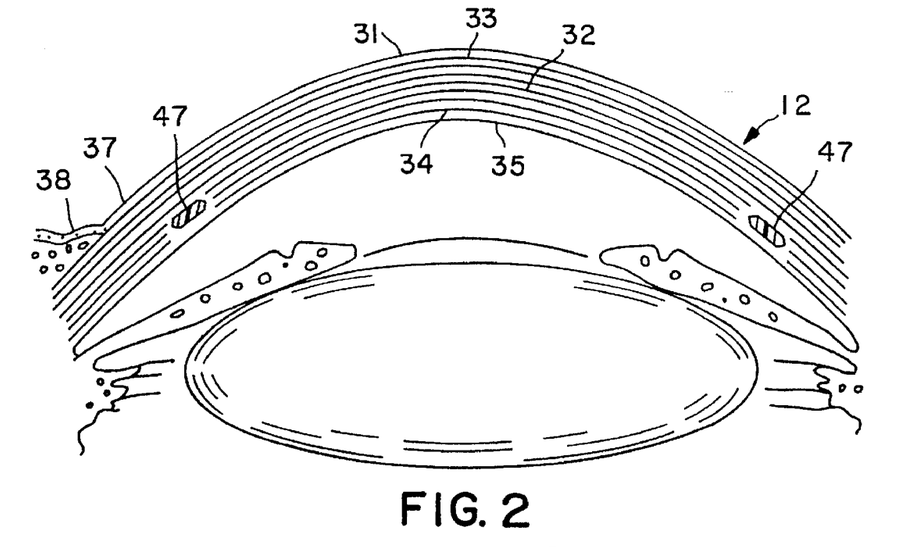
FIG. 2 is a schematic illustration of the anterior portion of the eye showing the various layers of the cornea.

Referring to FIG. 2, a more detailed drawing of the anterior portion of the globe shows the various layers of the cornea 12 comprising an epithelium 31. Epithelial cells on the surface thereof to act as a main protective layer of the cornea 12. These epithelial cells are rich in glycogen, enzymes and acetylcholine and their activity regulates the corneal corpuscles and controls the transport of water and electrolytes through the lamellae of the stroma 32 of the cornea 12.

An anterior limiting lamina 33, referred to as Bowman's membrane or layer, is positioned between the epithelium 31 and the stroma 32 of the cornea. The stroma 32 is comprised of lamella having bands of fibrils parallel to each other and crossing the whole of the cornea. While most of the fibrous bands are parallel to the surface, some are oblique, especially anteriorly. A posterior limiting lamina 34 is referred to as Descemet's membrane. It is a strong membrane sharply defined from the stroma 32 and resistant to pathological processes of the cornea.

The endothelium 36 is the most posterior layer of the cornea and consists of a single layer of cells which aid in maintaining the transparency of the cornea. The limbus 37 is the transition zone between the conjunctiva 38 and sclera 13 on the one hand and the cornea 12 on the other. An intrastromal corneal ring 47 is shown inserted between the stroma 32 of the cornea 12.

Figure 3:
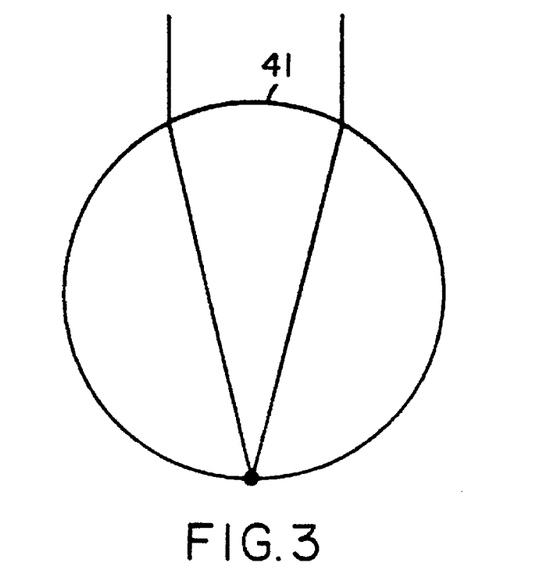
FIG. 3 is a schematic representation showing how light focuses on the retina of a normal eye.
Figure 4:
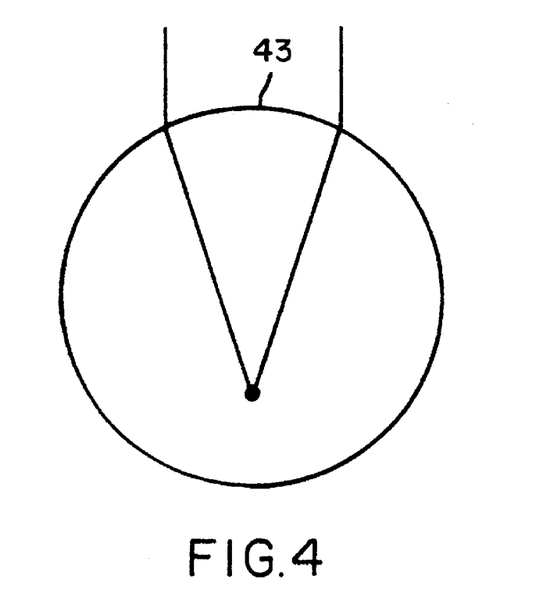
FIG. 4 is a schematic representation of how light does not focus on the retina of a myopic eye.

FIG. 3 shows the globe of the eye having a cornea 12 with a normal curvature 41. If parallel rays of light pass through the corneal surface of FIG. 3, they are refracted by the corneal surfaces to converge eventually near the retina of the eye. The diagram of FIG. 3 discounts, for the purposes of this discussion, the refractive effect of the lens or other portions of the eye. The eye depicted in FIG. 4 is myopic. The corneal curvature 43 causes the light rays to refract into focus at a point in the vitreous body which is short of the retinal surface. If an ICR is implanted into the chord of the cornea such that the radius of curvature of the cornea is uniformly increased, the central curvature of the cornea is flattened. Light rays refracted by the now flattened corneal surface will be refracted at a smaller angle and thus converge at a more distant point such as directly on the retina.

The ICRs of the present invention make it possible to adjust the radius of curvature of the cornea without adversely affecting its natural asphericity. By varying parameters of the ICR such as its thickness, shape and circumference the shape of the cornea can be changed in any desired manner. Where there is serious astigmatism, the natural asphericity will not be altered such that the astigmatism will be significantly increased. However, where there is significant astigmatism that results in impaired vision, the ICR of the invention may actually improve the asphericity to reduce such astigmatism and improve vision.

Figure 7:
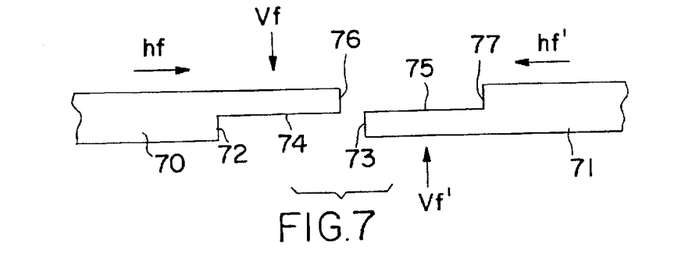
Figure 7A:
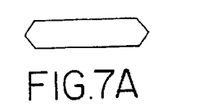
FIGS. 7A, 7B and 7C are views of the same embodiment with rings having different cross sectional configurations.

As shown in FIG. 2, an intrastromal corneal ring (ICR) 47, having a cross sectional shape as shown in FIG. 7A is shown implanted in the stromal layer of the cornea. By selecting the thickness of the ring according to the amount of correction necessary, the rays refracted by the cornea and other eye components can be brought to focus directly on the retina 18 (see FIGS. 3 and 4).

Figure 5:
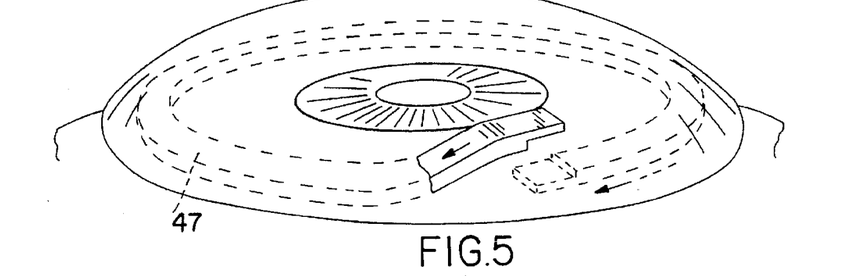
FIG. 5 is a perspective view of one embodiment of the ICR of the invention inserted within a cornea of a human eye.

FIG. 5 shows a perspective view of the ICR 47 inserted within a cornea 50 of a human eye. In the embodiment shown within FIG. 5, the ICR is placed in a manner such that the widest edge faces outward along the line of sight and away from the eye, whereas the narrower edge faces radically inward toward the center of the eye and the wide and narrow edges are perpendicular to each other. However, it should be noted that other configurations are possible.

Figure 6A:
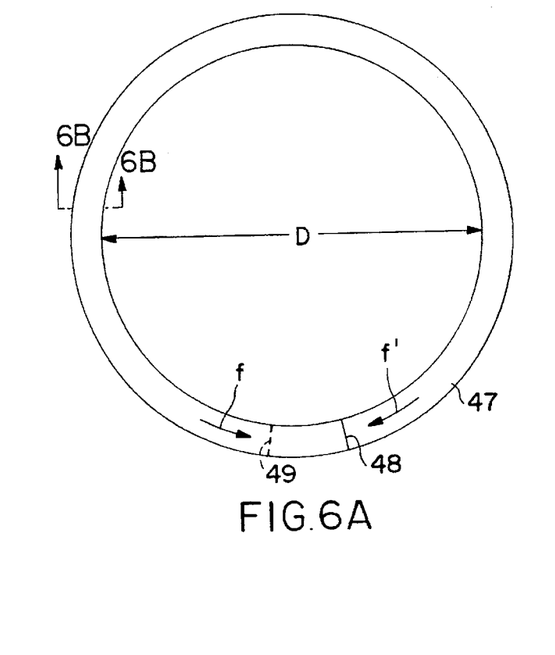
FIG. 6A includes a plane view and FIG. 6B a perspective sectional view of an ICR of the invention.
Figure 6B:
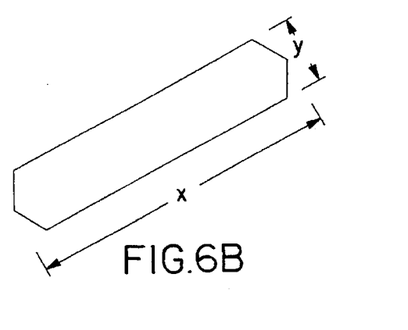

A planar view of the ICR 47 of the invention is shown in FIG. 6A. As shown, the ICR is circular in shape and is comprised of an elongated, circular, flexible body member. One possible cross sectional configuration is shown in FIG. 2 which configuration is basically rectangular with the outer sides being slightly bowed or pointed outward. Other cross sectional configurations are possible, such as rectangular, square, circular, triangular, and variations therebetween (see FIGS. 7A, 7B, 7C, 8B, 9A, 9B and 9C). Because the ring is circular, it has the same diameter in all directions. However, it is possible to configure the body of the ring in other slightly noncircular configurations (not shown), e.g., ovals and elongated ovals. In its preferred circular configuration, the diameter is slightly smaller than the size of a human cornea which is approximately 1 cm in diameter. The ring is comprised of a biocompatible material such as a biocompatible polymer which does not cause an immune reaction when brought into continuous contact with ocular tissues such as the corneal tissue. For example, the materials used in the construction of various types of contact lens including hard, soft and extended wear contact lens can be used in making ICRs of the invention. It will be understood by those skilled in the art that when the intrastromal rings of the invention are inserted in the cornea of the eye a certain degree of discomfort as well as inflammation and/or other reactions may occur. However, after a given adjustment period the adverse effects should be eliminated. In order to minimize any initial adverse effects the material should be nontoxic, biologically benign, and be relatively flexible as compared with a material such as metal. It is important to use materials which do not create a type of immune reaction or other adverse side effect when inserted into ocular tissue.

The ring in FIG. 6A shows one end 48. Because FIG. 6A is a planar view, the end 48 is shown as a single line. The other end 49 is shown by a dotted line in that this end is visible only from the other side of the ring 47. The ends 48 and 49 may be structured in several different configurations, as discussed further below. As shown in FIG. 6A, the ends 48 and 49 are overlapping each other and are forced toward each other as shown by the arrows f and f' which forces provide sufficient force within the horizontal plane of the ring such that the ends of the ring are in intimate contact with each other, providing a continuous, smooth and uninterrupted connection. The ring may also be configured such that the end portions of the ring force toward each other in vertical upward and downward directions so as to further increase the intimacy of the two ends which feature is described further below.

The thickness of the ring may be between 0.05 mm and 1.5 mm. Such a ring placed approximately at the 8 mm chord of the cornea provides a means for making a corrective adjustment to the focal point of light on the retina.

As indicated above FIGS. 5 and 6A show an ICR of the invention which is comprised of a generally circular body member. The ring is comprised of a material which has sufficient stiffness to maintain its generally circular shape the material is preferably a flexible solid and not a liquid or gel. Suitable materials include those which are used in making contact lens. The material should have properties that render it physiologically compatible with the tissue of the cornea. An illustrative material is a plastic type material sold under the trade name of PLEXIGLASS™, however many other biocompatible polymers are useful in the invention, including but not limited to polyolefins (e.g., polypropylene and polybutylene), polycarbonates, acrylic resins (e.g., acrylates and methacrylates, including polymethylmethacrylate (PMMA) and polyhydroxyethyl methacrylate (polyHEMA)), polyacetals, polyesters, polyamides (e.g., nylon), polyurethanes, epoxy resins, silicones or other natural or synthetic rubbers, copolymers that are composed of hard and soft segments (e.g., HYTREL, Dupont, Wilmington, Del.), polytetrafluoroethylene (PTFE), polyvinylpyrrolidone, polyethers/ether ketones, polysulfones, glass, and copolymers (discrete or block), blends and mixtures of the above. As discussed above, cross sectional shape of the rings can vary. When a cross section of the ring is circular, it is generally dimensioned to be about 0.05 mm to 1.00 mm in thickness, and about 0.5 to 1.0 cm in diameter.

The cross sectional configuration shown within FIG. 2 is schematically shown in FIG. 7A. When this configuration is used, the dimension shown from point to point (dimension x) is within the range of approximately 0.5 mm to 3.25 mm and the thickness (dimension y) is generally in the range from about 0.05 mm to about 1.5 mm.

There are a number of factors which affect the degree of flattening of the cornea obtained depending on the thickness of the ring being inserted. Accordingly, it is not always possible to deduce a direct relationship between the ring thickness and the degree of flattening and therefore the change of focal point. Variations are caused by factors such as the type of mammal in which the ring is being inserted and the size and shape of the eye. However, in certain experiments it has been found that optical corrections can be carried out at the rate of 1 diopter of flattening for each 0.02 mm increase in ICR thickness when the size of the ICR is in the range of about 0.26 mm to about 0.46 mm in thickness.

Even where the eye is not myopic, the ICRs of the present invention may be useful to alleviate excessive astigmatism.

A typical panel of ICRs will consist of 5 ICRs with the following thicknesses: 0.25 mm, 0.30 mm, 0.35 mm, 0.40 mm and 0.45 mm. The corrective refraction for those ICRs are as follows: between 1.0 and 3.0 diopters for the 0.25 mm ICR, between 2.0 and 5.0 diopters for the 0.30 mm ICR, between 2.0 and 8.0 diopters for the 0.35 mm ICR, between 3.0 and 10.0 diopters for the 0.40 mm ICR, and between 4.0 and 15.0 diopters for the 0.45 mm ICR. It should be noted that these values are for ICRs can range from 0.05 to 1.0 mm in thickness and obtain correction of from 0.5 to 18.0. The amount of corrective refraction for the various thicknesses of ICRs of different cross sectional shaped rings may differ from those values depending on the individual patient and variety of factors.

The ICR is inserted into the corneal stroma of the eye through a 2.5 mm oblique keratotomy incision placed peripherally into the corneal stroma. The size of the insertion will vary somewhat depending on factors such as the size of the ring being inserted. In general, the size of the insertion is approximately 0.5 mm to 5.0 mm in length with an incision of approximately 2.5 mm being typical. Prior to ring insertion, a channeling blade is inserted at the depth of the incision and a circular channel is cut into the corneal stroma. Proper centering of the cut is accomplished by use of a centering device that aligns the channeling blade. The ring is then inserted and the ends are secured by the overlapping end portion which may be supplemented by fastening one end to the other. However, such fastening is not generally necessary as the end portions are designed so that further fastening is not required.

SPECIFIC PREFERRED EMBODIMENTS

Seven different basic preferred embodiments are shown in FIGS. 7–13. In addition, many of the basic embodiments are further illustrated by means of subembodiments which include, for example, different configurations of the cross sectional parameter of the ring. It is emphasized that each of the embodiments and subembodiments may be interchanged and be comprised of different materials and provided in different sizes in accordance with the size limitations indicated above. Further, the disclosures of these different embodiments may demonstrate to others skilled in the art that other embodiments are possible which provide substantially the same results in terms of providing a ring structure whereby the ends of the rings can be interconnected without an additional component and/or can be interconnected so as to provide a substantially smooth and continuous interconnection. Although the embodiments of the invention generally do not use any additional components at least one embodiment (see FIG. 13) includes an overlapping sleeve which covers the connected end portions and results in a substantially smooth and continuous interconnection.

Referring now to FIG. 7 which is a cross sectional view of a notched overlapping embodiment which shows the ring end portions 70 and 71 separated from each other. The end portion 70 includes a surface 72 which will be contacted by the surface 73 of the end portion 71. Further, the surface 74 will be brought into intimate contact with the surface 75. In a similar manner the surface 76 will be contacted intimately with the surface 77. The opposing surfaces are forced together as indicated by the horizontal and vertical force arrows. Specifically, the horizontal force arrow hf pointing towards the right and the opposing horizontal force arrow hf' points towards the left. This is accomplished by the structure of the ring itself. The vertical force arrows vf pointing upward and vf' pointing downward force the surfaces 74 and 75 together in the same manner that the horizontal forces bring the surfaces 72 and 73 together as well as the surfaces 77 and 76.

Figure 7B:
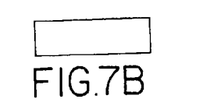
Figure 7C:
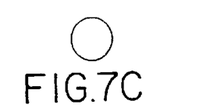

The basic embodiment shown within FIG. 7 can be configured using different ring structures such as shown by the different cross sectional ring configurations of FIGS. 7A, 7B and 7C which include a rectangular cross section with points bowing outward from each short side, a rectangular cross section and a circular cross section respectively.

Figure 8:
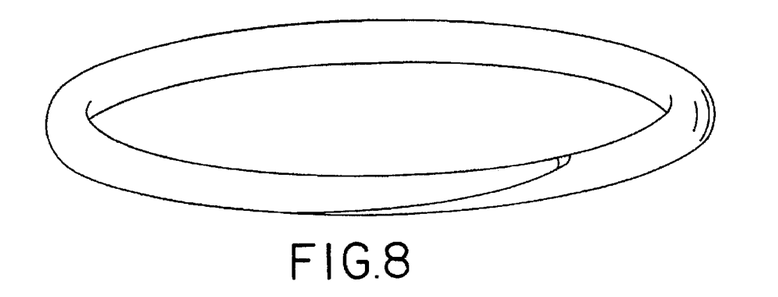
Figure 8A:
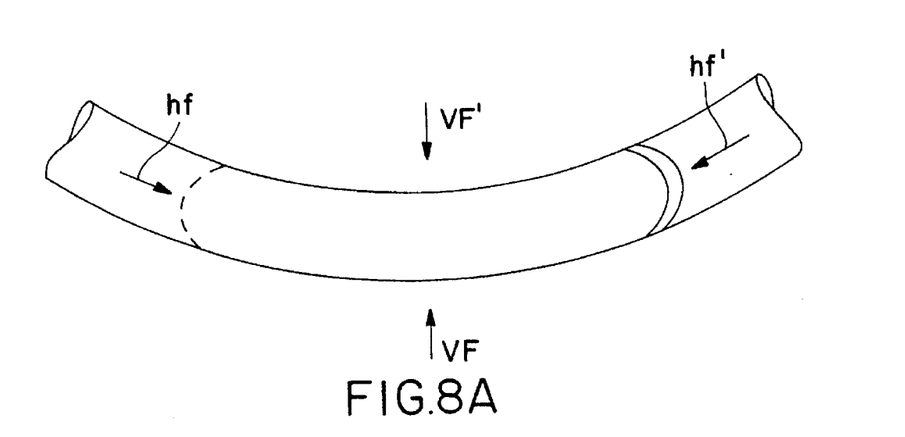
Figure 8B:
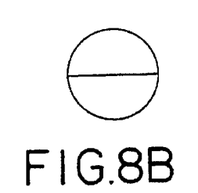
Figure 8C:
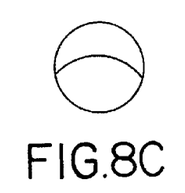
Figure 8D:
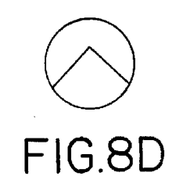
Figure 8E:
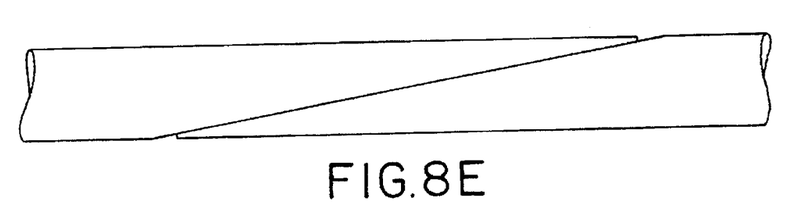
FIG. 8E is a longitudinal cross sectional view showing the overlapping ring ends.

FIG. 8 shows a tapered overlapping configuration. The tapered effects of the end portions 80 and 81 is dramatically shown within FIG. 8E. One end portion 80 gradually narrows at the same rate and in the apposite direction that the end portion 81 narrows. The end portions 80 and 81 are held together by horizontal and vertical force vectors which oppose each other and are shown as hf, hf', vf and vf' as shown in FIG. 8A. The cross sectional structure of the ring can be circular as indicated by the different configurations in FIGS. 8B, 8C and 8D. However, as shown in these figures the manner in which the end portions 80 and 81 fit together along their adjacent surfaces can vary from the planar interconnection of FIG. 8B to the curved plane of FIG. 8C and the peaked interconnection of FIG. 8D. A cross section is shown in FIG. 8E.

Figure 9:
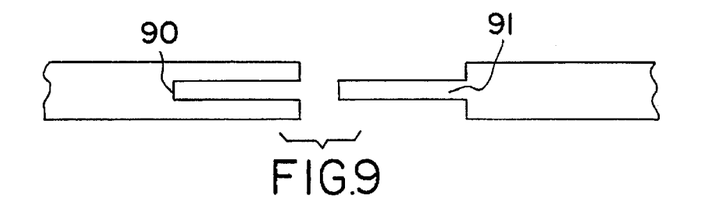
FIG. 9 is a perspective view of a plug and socket embodiment with FIGS. 9A, 9B and 9C showing different outer ring configurations
Figure 9A:
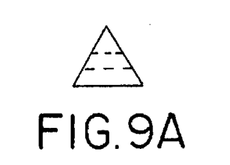
Figure 9B:
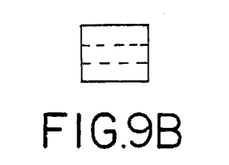
Figure 9C:
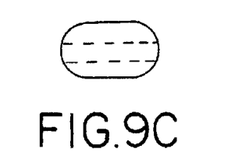
Figure 9D:
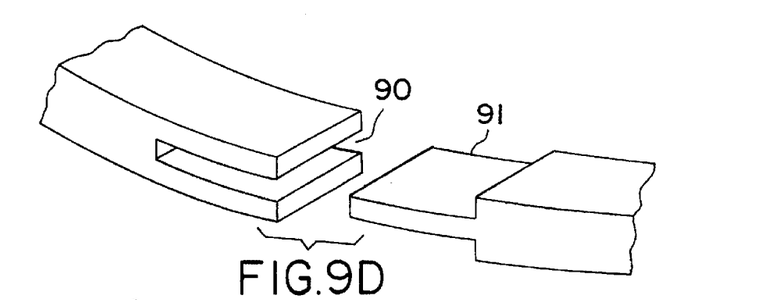
FIGS. 9D, 9E and 9F show variations of the embodiment.
Figure 9E:
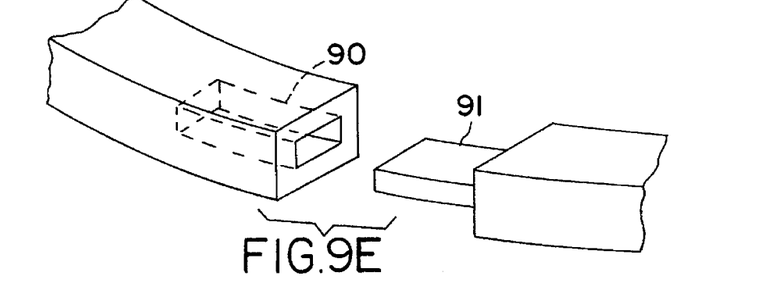
Figure 9F:
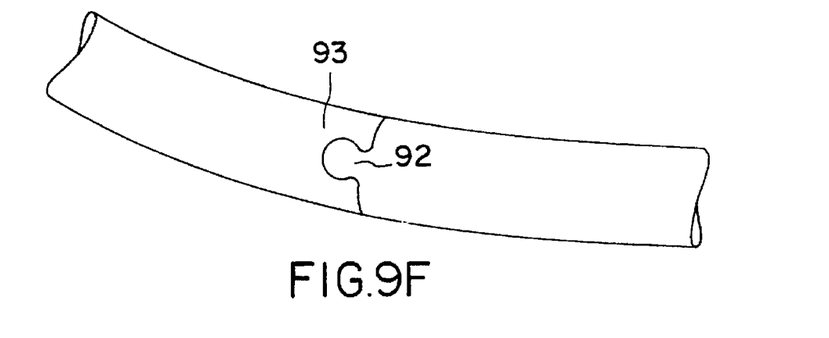

FIG. 9 shows a plug and socket interconnection. The plug end portion 91 fits securely within the socket end portion 90. When the two ends are securely interconnected the surface of the ring provides a substantially smooth and continuous interconnection. The cross sectional configuration of the ring may be triangular, square, or oval as shown in FIGS. 9A, 9B and 9C or include variations thereof. Further, the socket may be closed on all sides (FIG. 9E) or open on two sides (FIG. 9D). The socket end can securely hold the plug end in place and prevent the ends from separating. In FIG. 9F another variation of a plug and socket embodiment is shown. The plug 92 has a tear drop-like shape and fits in the socket 93 when the end portions are forced toward each other.

The configurations of FIGS. 7, 8 and 9 are preferred due to their simplicity. However, these configurations do not provide constructions whereby the ends of the rings are securely held in place in the event of separational forces. (The embodiment of FIG. 9F does provide some resistance to separational forces.) The following configurations shown in FIGS. 10, 11, 12 and 13 do provide some additional complexity in terms of their structure. However, these structures do result in holding the ring ends together even if the ring ends are subjected to separational forces.

Figure 10:
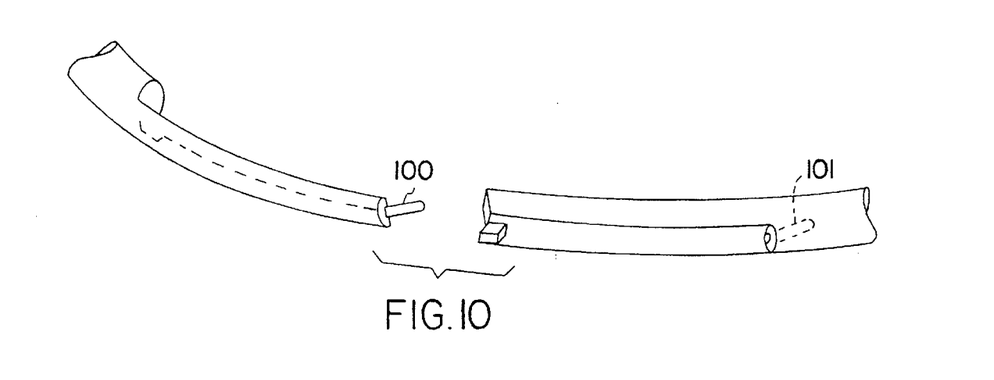
FIG. 10 is a cross sectional view of an overlapping interlocking ring embodiment with FIGS. 10A and 10B showing how the ends fit together.
Figure 10A:
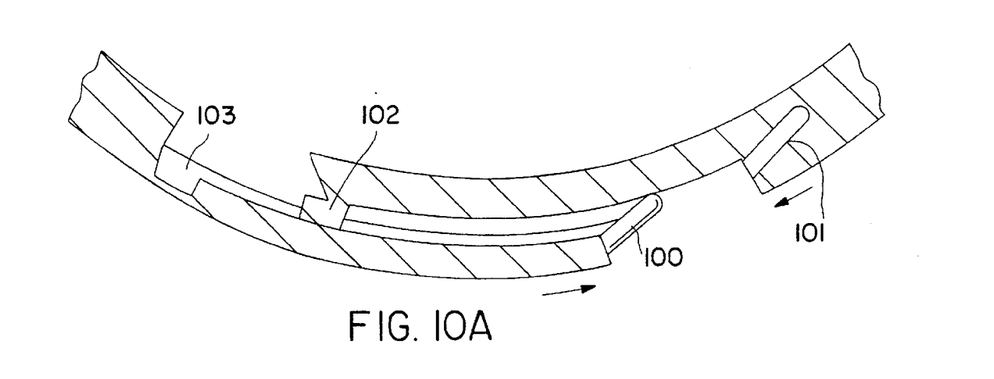
Figure 10B:
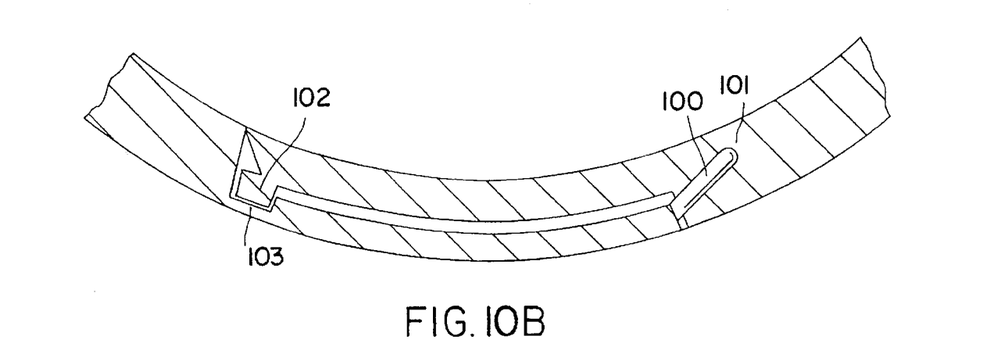

The configuration shown in FIG. 10 provides overlapping ends which are notched in the same manner as shown within FIG. 7. However, the overlapping end surfaces include an additional corresponding plug 100 and socket 101 into which the opposing pieces fit and snap the opposing pieces securely into place. Preferably, the plug 100 is slightly larger in diameter than is the diameter of the socket 101. Due to the slight variation in size, the plug 100 will fit securely within the socket 101 and be held securely in place. The ends may further include a protuberance such as the protuberance 102 which fits within the depression 103. In a similar manner, the protuberance 102 may be slightly larger in one dimension than is the depression 103, so that a tight fit is provided for. FIG. 10A shows the ends moving towards each other and FIG. 10B shows the ends interlocked into each other.

Figure 11A:
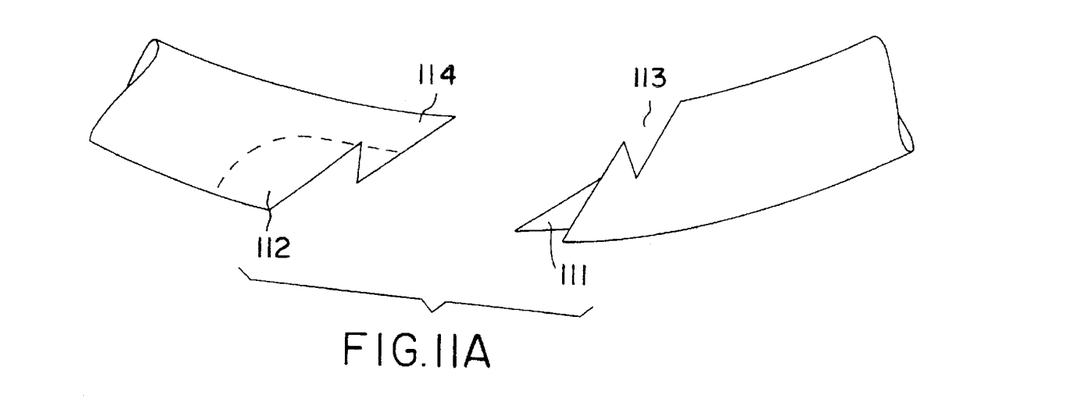
FIGS. 11A, 11B and 11C are cross sectional views of an overlapping notched interlocking embodiment with a blade.
Figure 11B:
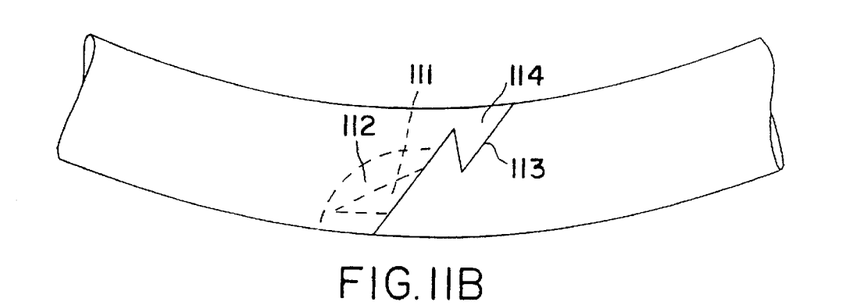
Figure 11C:
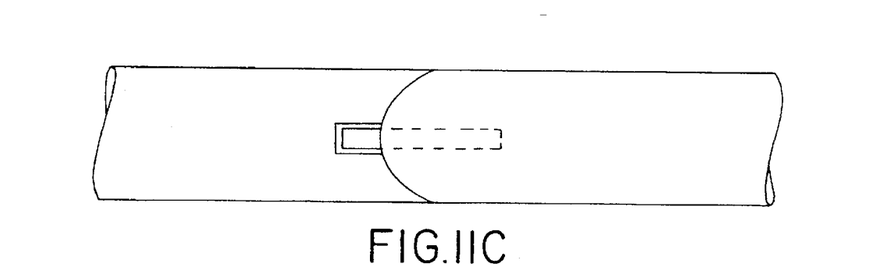

The embodiment shown in FIG. 11 provides an additional advantage in that the end of the ring can be used to separate the stroma of the cornea and create an annular channel. The blade or stroma separation endpiece 111 is positioned on the end of the ring and is inserted into a socket 112 on the opposing end portion of the ring. The notches 113 and 114 on each ring lock the ends into place and prevent the ring from opening.

Figure 12A:
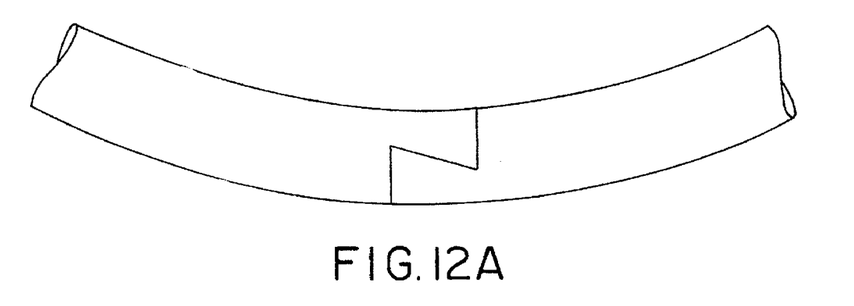
Figure 12B:
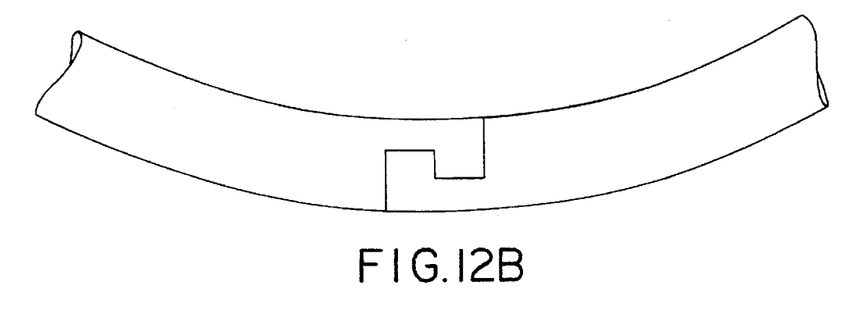

FIGS. 12A and 12B show triangular and rectangular notched ring ends which ends are constructed so that they securely fit one into the other. In accordance with this embodiment the notches on sockets may be designed so that the socket is somewhat smaller than the notch thereby providing for a tight fit. However, such is not necessarily required in that the ends of the ring will be forced together vertically and horizontally by force vectors as shown within FIG. 7.

Figure 13:
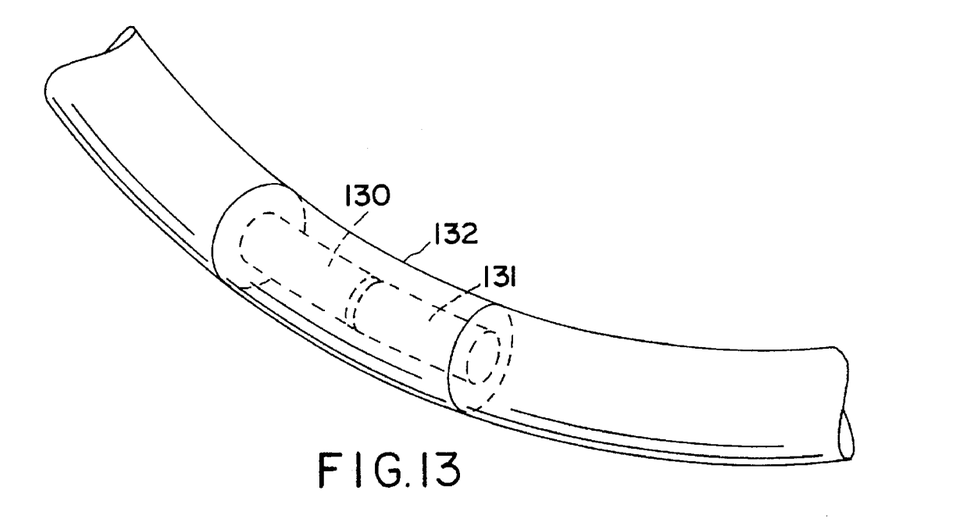
FIG. 13 shows a shrink tube connector embodiment.

FIG. 13 shows end portion 130 and 131 which each have a reduced diameter and have their ends forced toward each other. A shrinkable or elastic sleeve 132 fits around the ends 130 and 131 and has a thickness which is equal to the difference in thickness between the body of the ring and the end portions. Thus, when the sleeve is in place the connection is smooth and continuous.

Modifications of the above described modes for carrying out the invention may occur to persons of skill in the fields of medicine, ophthalmology, optometry and/or related fields upon reading the disclosure and are all intended to be within the scope of the following claims.

We claim:

1. A method for implanting an intracorneal ring in an eye, comprising the steps of:

placing a split ring having first and second end portions in the cornea of the eye; and coupling together the first and second end portions such that they form a substantially smooth and continuous ring surface.

2. The method of claim 1, including forming an annular channel in the cornea for placing the ring therein.

3. The method of claim 2, including cutting an initial incision into the cornea, the channel forming step including forming the channel from the incision.

4. An intracorneal ring for adjusting the shape of the cornea of an eye, comprising first and second end portions, said end portions being spaced from one another when in a first state and coupled to one another in a manner which forms a substantially smooth and continuous ring surface in the vicinity of the coupling when in a second state.

5. The intracorneal ring of claim 4, wherein said end portions overlap when in said second state.

6. The intracorneal ring of claim 5, wherein said first end portion comprises at least one notch and said end portion has at least one protuberance corresponding to said at least one notch.

7. The intracorneal ring of claim 4, further comprising an interconnecting portion for coupling the end portions.

8. The intracorneal ring of claim 4, wherein said ring is flexible.

9. The intracorneal ring of claim 4, wherein said ring is generally circular.

10. The intracorneal ring of claim 4, wherein said ring is comprised of biocompatible material.

* * * * *